(12) United States Patent
Wu et al.

(10) Patent No.: US 6,848,827 B2
(45) Date of Patent: Feb. 1, 2005

(54) METHOD AND APPARATUS FOR CALIBRATING DETECTOR SPECTRAL RESPONSE

(75) Inventors: Xiaoye Wu, Rexford, NY (US); James LeBlanc, Niskayuna, NY (US); Deborah J. Walter, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/437,222

(22) Filed: May 13, 2003

(65) Prior Publication Data

US 2004/0228451 A1 Nov. 18, 2004

(51) Int. Cl.[7] .............................................. G01D 18/00
(52) U.S. Cl. ........................................ 378/207; 378/19
(58) Field of Search ............................ 378/18, 19, 207

(56) References Cited

U.S. PATENT DOCUMENTS 4,897,788 A * 1/1990 King ........................... 378/12
5,214,578 A * 5/1993 Cornuejols et al. ......... 378/207
5,774,519 A * 6/1998 Lindstrom et al. ........... 378/18

* cited by examiner

Primary Examiner—Craig E. Church
Assistant Examiner—Jurie Yun
(74) Attorney, Agent, or Firm—Fletcher Yoder (57) ABSTRACT

The present technique provides for the spectral calibration of the detector elements of a CT detector using one or more offset calibration phantoms. The offset phantoms provide greater coverage of the detector elements as well as spectral response data associated with penetration lengths ranging in length from a minimum chord of the phantom to the diameter of the phantom. The spectral response as a function of penetration length can be obtained for each detector element by comparing the fitting of each projection view to the corresponding measured projection view over all view angles. The fitting information may then be employed to derive the coefficients of the spectral response curve for each detector element, which may in turn be employed to provide rapid correction of the spectral response for each element.

45 Claims, 7 Drawing Sheets

METHOD AND APPARATUS FOR CALIBRATING DETECTOR SPECTRAL RESPONSE

BACKGROUND OF THE INVENTION

The present invention relates generally to the field of medical imaging. In particular, the following techniques relate to computed tomography imaging systems and the calibration of detectors used in such systems.

Computed tomography (CT) imaging systems measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced projection images. A CT system produces data that represents the line integral of linear attenuation coefficients of the scanned object. This data is then reconstructed to produce an image, which is typically displayed on a cathode ray tube, and may be printed or reproduced on film. A virtual 3-D image may also be produced by a CT examination.

CT scanners operate by projecting fan shaped or cone shaped X-ray beams from an X-ray source that is collimated and passes through the object, such as a patient. The attenuated beams are then detected by a set of detector elements. The detector element produces a signal based on the intensity of the X-ray beams, which are attenuated by the patient, and the data are processed to produce signals that represent the line integrals of the attenuation coefficients of the object along the ray paths. These signals are typically called projections. By using reconstruction techniques, such as filtered backprojection, useful images are formulated from the projections. The locations of pathologies may then be identified either automatically, such as by a computer-assisted diagnosis (CAD) algorithm or, more conventionally, by a trained radiologist. CT scanning provides certain advantages over other types of techniques in diagnosing disease particularly because it illustrates the accurate anatomical information about the body. Further, CT scans may help physicians distinguish between types of abnormalities more accurately.

In order to accurately reconstruct CT images, the spectral response of each detector element is calibrated to a standardized spectral response. Spectral calibration is useful in removing artifacts, such as beam-hardening artifacts, which may occur when tissue is imaged. In particular, the beam-hardening phenomena may cause nonuniformities in a reconstructed image of a uniform object, such as the phantoms used in calibration. This phenomenon, known as "cupping effect," arises due to the polychromatic nature of the X-ray beam and the resulting differential absorption of high and low energy components of the beam. Correction factors to the projection data may be applied to remove the beam hardening artifacts in the reconstructed image.

One method to determine the correction factors is through empirical experimentation. The determination of the correction factors can be made though either system modeling with a nominal detector spectral response or though experiments by adjusting the correction coefficients such that the reconstructed image of a water phantom, for example, becomes uniform. With such a beam hardening spectral correction, the resulting reconstructed image, however, may still contain ring or band artifacts due to the differential spectral response of the various detector elements. The term "spectral error," as used herein, refers to the differential detector spectral response as compared to a nominal channel responding to an incident polychromatic x-ray spectrum. The spectral calibration process generates correction functions for each detector element to balance channel-to-channel response to an X-ray signal, thereby removing the ring or band artifacts. Various factors, however, may result in the derivation of correction functions from the spectral calibration process that are insufficient or inadequate to fully remove artifacts in the reconstructed image resulting from differential detector element response. In particular, the techniques employed to derive correction functions typically rely upon an insufficient number of data points representing the spectral response of an element as a function of projection value. As a result, the correction function for detector channel-to-channel variation in spectral response may be substantially linear, even though the spectral response of a detector element as a function of projection value is not necessarily linear.

For example, spectral calibration may be performed by positioning a circular phantom at the isocenter of an imaging system. The symmetry of the phantom in conjunction with the position at the isocenter results in attenuation data being collected which provides limited detector channel coverage and which corresponds to a single penetration length, i.e., the distance traversed by the X-rays through the attenuating object. As a result, calibration data are acquired at each detector element for a single penetration length for each phantom and do not provide information about detector spectral response as a function of X-ray penetration length. A calibration may be performed using a second phantom to acquire a data point at a second penetration length for each detector element such that a linear correction function may be derived. Likewise additional calibrations may be performed to provide additional data points. The resulting correction function, however, is generally substantially linear and may fail to adequately correct the differential spectral responses of the detector elements to the extent that such responses are non-linear away from the measured data points. In addition, the image regions corresponding to the joining of the different data sets may give rise to image artifacts.

One technique, which may be employed to address these concerns, includes smoothing projections from the measured phantom calibration data to extract baseline projections, which may be used to determine correction factors for each detector element. In particular, the smoothed projection may be considered an ideal projection to which the detector elements may be calibrated. This technique, however, may be unreliable if the detector elements differentially introduce large relative spectral errors, which influence the computation of the smoothed projections, resulting in the extraction of an incorrect baseline. A technique for measuring spectral errors as a function of X-ray projection value and of calibrating detector elements to reduce the incidence of image artifacts attributable to differential channel-to-channel spectral response is therefore desirable.

BRIEF DESCRIPTION OF THE INVENTION

The present technique provides a novel approach for the spectral calibration of the detector elements of a CT detector using one or more calibration phantoms offset from isocenter. The offset phantoms provide greater coverage of the detector elements and provide spectral response data for a range of penetration lengths for each detector element. The penetration lengths range in length from a minimum chord of the phantom, determined by the offset distance and the diameter of the phantom, to the diameter of the phantom. For each detector element, the spectral response as a function of projection value can be obtained by comparing the fitting of each projection view to the corresponding measured projection view over all view angles. The fitting information may then be employed to derive the coefficients of the spectral response curve for each detector element, which may in turn be employed to provide rapid calibration of the spectral response for each element.

In one embodiment of the present technique, a method for calibrating a detector element of an imaging system is provided. The method comprises positioning a calibration phantom offset from the isocenter of an imaging system and performing a calibration scan of the offset calibration phantom. A measured projection data set is acquired for a detector element of the imaging system and the measured projection data set is pre-processed to generate a calibration projection data set for the detector element. A calibration vector for the detector element is derived from the calibration projection data set.

In another embodiment of the present technique, a program for calibrating a detector element of an imaging system is provided. The program comprises routines stored on tangible media including a routine for performing a calibration scan of a calibration phantom offset from the iso-center of an imaging system. The program also comprises a routine for acquiring a measured projection data set for a detector element of the imaging system and a routine for preprocessing the measured projection data set to generate a calibration projection data set for the detector element. In addition, the program comprises a routine for deriving a calibration vector for the detector element from the calibration projection data set.

In a further embodiment of the present technique, an imaging system is provided. The imaging system comprises a source of radiation and a detector array comprising a plurality of detector elements, configured to detect radiation from the source. The system also comprises a system controller configured to control the source and the detector array and to acquire data from the detector array. The system also comprises a computer configured to communicate with the system controller. The computer is configured to perform a calibration scan of a calibration phantom offset from the iso-center of the imaging system, to acquire a measured projection data set for each detector element of the imaging system, to pre-process the measured projection data sets to generate a calibration projection data set for each detector element, and to derive a calibration vector for each detector element from the respective calibration projection data set. The system also comprises an operator workstation configured to communicate with the computer.

DETAILED DESCRIPTION OF SPECIFIC EMBODIMENTS

Figure 1:
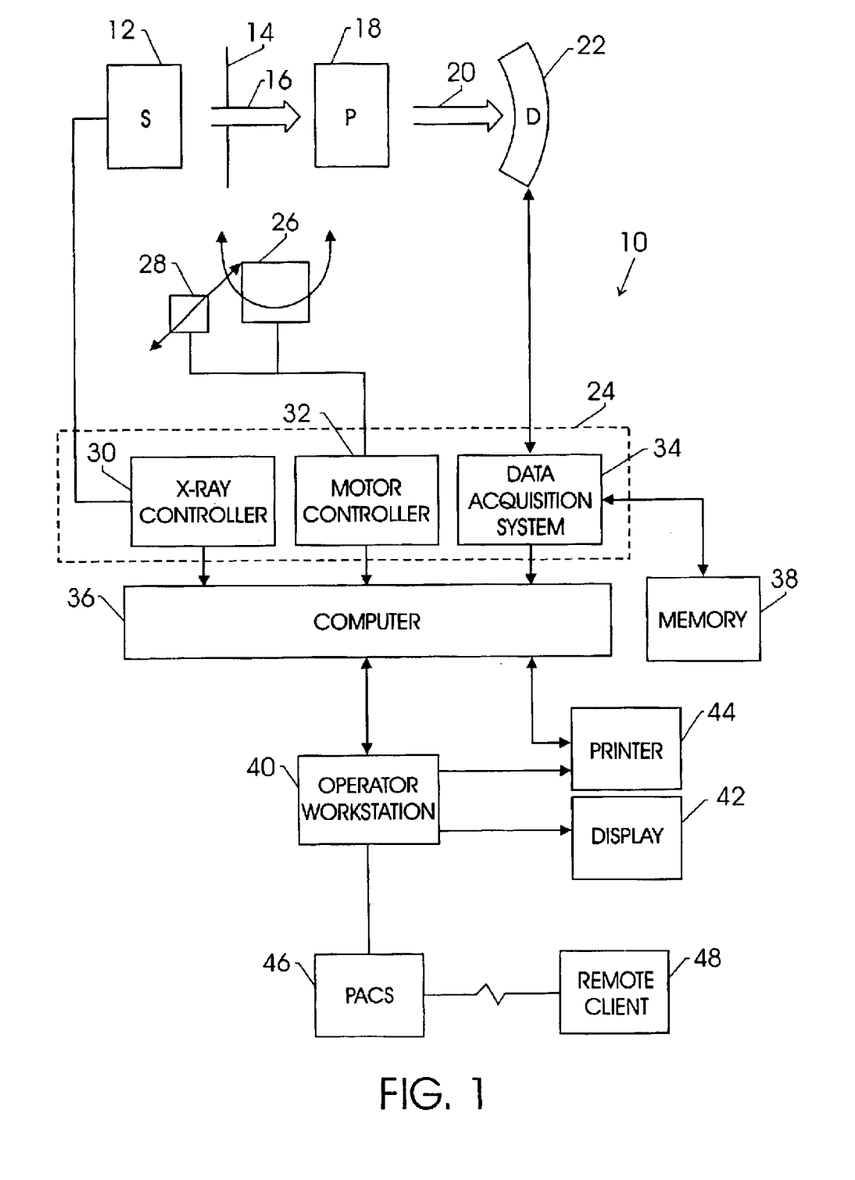
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a rotational subsystem 26 and a linear positioning subsystem 28. The rotational subsystem 26 enables the X-ray source 12, collimator 14 and the detector 22 to be rotated one or multiple turns around the patient 18. It should be noted that the rotational subsystem 26 might include a gantry. Thus, the system controller 24 may be utilized to operate the gantry. The linear positioning subsystem 28 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 26 and the linear positioning subsystem 28.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory to store a large amount of data might be utilized by such an exemplary system 10. Moreover, the memory 38 may be located at this acquisition system or may include remote components for storing data, processing parameters, and routines described below. Also the computer 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image and to control imaging. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image and to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
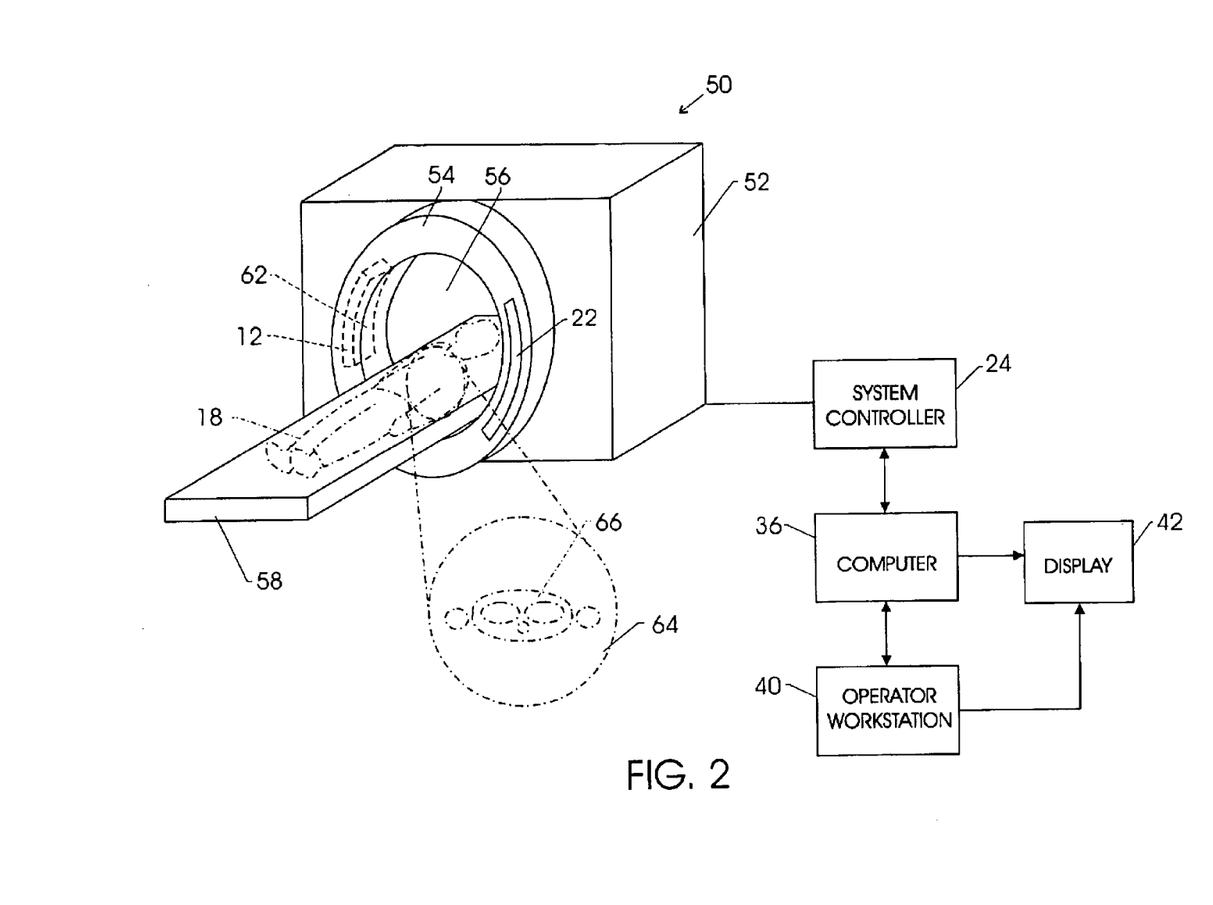
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is typically a multi-slice detector CT (MDCT) system that offers a wide array of axial coverage, high gantry rotational speed, and high spatial resolution, all of which allow the use of sophisticated cardiac reconstruction algorithms. The CT scanning system 50 is illustrated with a frame 52 and a gantry 54 that has an aperture 56. The aperture 56 may typically be 50 cm in diameter. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 26 (see FIG. 1). The gantry 54 is illustrated with the source of radiation 12, typically an X-ray tube that emits X-ray radiation from a focal point 62. For cardiac imaging, the stream of radiation is directed towards the heart of the patient 18.

In typical operation, X-ray source 12 projects an X-ray beam from the focal point 62 and toward detector array 22. The detector 22 is generally formed by a plurality of detector elements, which sense the X-rays that pass through and around a subject of interest, such as the heart and chest. Each detector element produces an electrical signal that represents the intensity of the X-ray beam at the position of the element at the time the beam strikes the detector. Furthermore, the gantry 54 is rotated around the subject of interest so that a plurality of radiographic views may be collected by the computer 36. Thus, an image or slice is computed which may incorporate, in certain modes, less or more than 360 degrees of projection data, to formulate an image. The image is collimated to desired dimensions, typically less than 40 mm thick using either lead shutters in front of the X-ray source 12 and different detector apertures. The collimator 14 (see FIG. 1) typically defines the size and shape of the X-ray beam that emerges from the X-ray source 12. In addition, a bowtie filter may be included in the system 50 to further control the patient dose. In particular, the bowtie filter pre-attenuates the X-rays to accommodate the body part being imaged, such as head or torso, such that, in general, greater attenuation is provided for X-ray passing through or near the isocenter 72. In this manner, the bowtie filter conforms the X-ray intensity during imaging in accordance with the region being imaged.

Thus, as the X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, are then filtered and backprojected to formulate an image of the scanned area. As mentioned above, the computer 36 is typically used to control the entire CT system 10. The main computer that controls the operation of the system may be adapted to control features enabled by the system controller 24. Further, the operator workstation 40 is coupled to the computer 36 as well as to a display, so that the reconstructed image may be viewed. Alternatively, some or all of the processing described herein may be performed remotely by additional computing resources based upon raw or partially processed image data.

Once reconstructed, the image produced by the system of FIGS. 1 and 2 reveals internal features of a patient. As illustrated generally in FIG. 2, the image 64 may be displayed to show these features, such as indicated at reference numeral 66 in FIG. 2. In traditional approaches to diagnosis of medical conditions, such as disease states, and more generally of medical events, a radiologist or physician would consider a hard copy of display of the image 64 to discern characteristic features of interest. Such features might include lesions, sizes and shapes of particular anatomies or organs, and other features which would be discernable in the image based upon the skill and knowledge of the individual practitioner. Other analyses may be based upon capabilities of various CAD algorithms with subsequent processing and data acquisition at the discretion of the practitioner.

Figure 3:
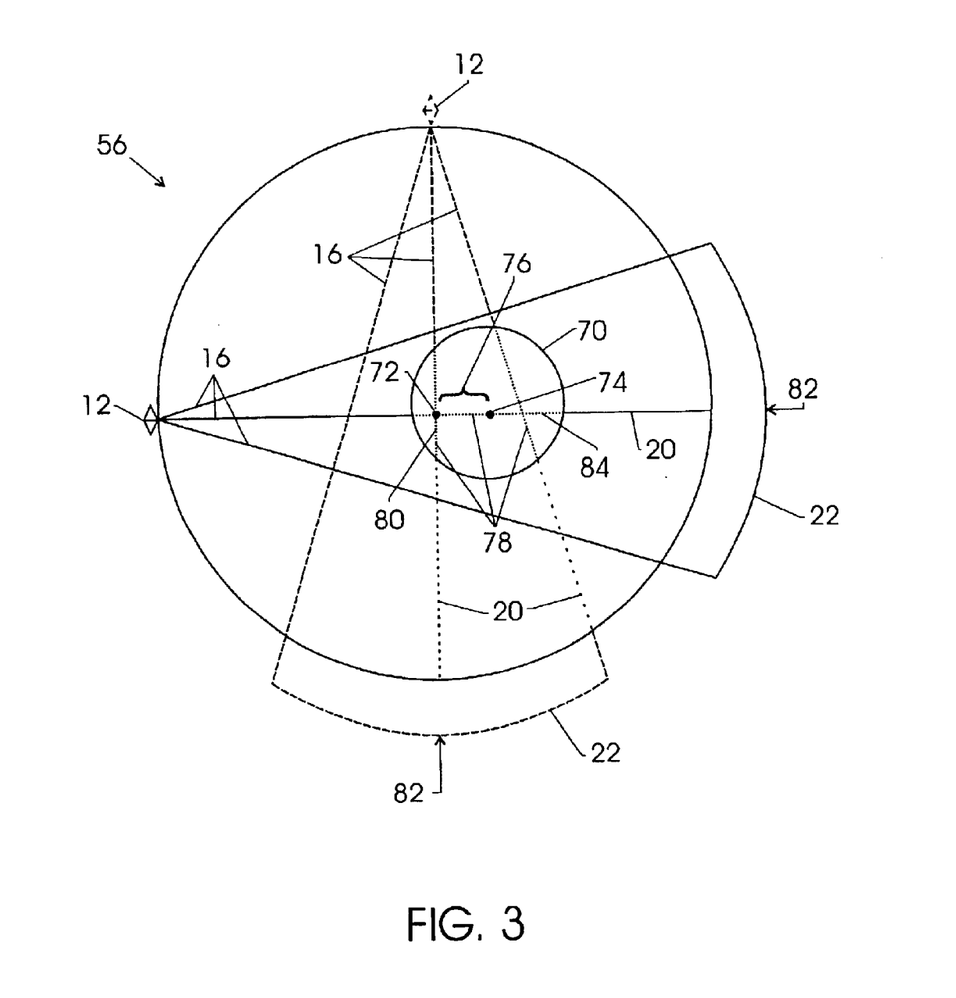
FIG. 3 is a diagrammatical view of a CT aperture in which a calibration phantom is offset from the aperture isocenter.

In order to eliminate ring and band artifacts related to the differential spectral response of the detector elements from the final reconstructed image, the detector 22 may undergo a spectral calibration process. Spectral calibration may be performed with X-ray modifiers such as the collimator 14 or bowtie filter present such that the calibration is applicable to diagnostic imaging conditions. The spectral calibration process may be accomplished by acquiring attenuation data associated with a circular phantom 70 that is offset from the isocenter 72 between the source 12 and the detector 22, as depicted in FIG. 3. A phantom 70 may be considered offset from the isocenter 72 when the center 74 of the phantom 70 is not coincident with the isocenter 72. In general, the offset may be defined by the offset distance 76 between the respective phantom center 74 and the isocenter 72.

The phantom 70 may be composed of water or of another material similar to water in mass-absorption characteristics such that the phantom 70 attenuates X-rays 16 which pass through in proportion to the penetration length 78, i.e., the distance an X-ray travels through the phantom 70. Because the phantom 70 is offset from the isocenter 72, a single phantom, with the proper offset, can effectively cover a large detector region that would otherwise require two or more phantoms for satisfactory spectral calibration results.

The present technique, however, may be performed with additional phantoms 70 and additional calibration scans to ensure the effectiveness of the derived correction functions. In particular, the data obtained from imaging two differently sized calibration phantoms 70 may be combined to provide more extensive information regarding spectral response as a function of penetration length and to provide data points for additional detector elements. For example, the combined data may allow the generation of a more comprehensive spectral response curve or function within the calibration range. Additional phantoms employed may be composed of different materials as opposed to techniques which require multiple phantoms to share a common composition.

Figure 4:
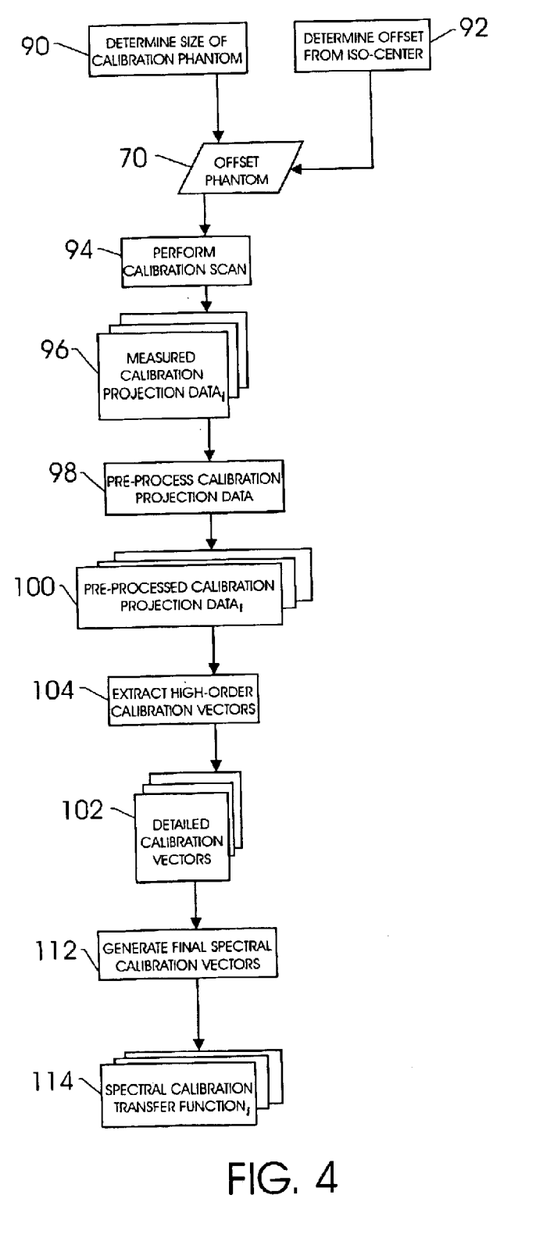
FIG. 4 is a flowchart depicting one embodiment of the present technique.

Referring to FIG. 4, the size of the phantom may be determined, as represented by step 90, based upon several factors, such as the maximum X-ray penetration length 84 and number of detector channels to be covered. These factors are generally related to the diameter of the phantom 70. Because a number of outlying detector elements do not acquire signals attenuated by the phantom in any view, spectral corrections in this outlying region are potentially erroneous. However, since the effect of spectral errors for detector elements far from isocenter are diluted by projections from many other detector elements during the reconstruction process, the lack of calibration for those detector elements may not cause noticeable image artifacts.

For example, in one embodiment, for calibration consistent with cranial imaging, a head bowtie filter and a small phantom 70 such as 20–25 cm in diameter, may be employed. Similarly, for calibration consistent with torso imaging, a body bowtie filter and a large phantom, such as 35 cm in diameter, may be employed. Phantoms 70 with diameters smaller than 20 cm may also be employed in some instances such as for pediatric imaging. Other sizes of phantoms 70 may of course be employed as desired in order to obtain the desired coverage for spectral calibration.

Likewise, at step 92, the offset distance 76 may be determined based upon the size of the phantom 70 employed as well as the desired degree of detector coverage. In general, to obtain greater detector coverage, the offset distance 76 is increased. However, as the offset distance 76 increases, detector elements near the center of the detector 22 may acquire insufficient calibration data. In particular, as depicted in FIG. 3, as the source 12 and detector 22 rotate around the isocenter 72, some elements of the detector 22 which measure X-rays passing near the isocenter may be measuring unattenuated X-rays during part of the rotation, resulting in less calibration data for these "near-iso" channels. Because the "near-iso" channels are highly sensitive to spectral artifacts due to their disproportionately large contribution to the reconstructed image, it may be undesirable to reduce the amount of calibration data acquired by these near-iso channels.

It is, therefore, desirable to balance the desired degree of detector coverage with the desired amount of calibration data obtained by near-iso channels. In one embodiment, this is accomplished by selecting an offset distance 76 such that a minimum penetration length 80 of 12 cm to 15 cm results, as measured by the "iso" channel 82, i.e., that channel which measures X-rays passing through the iso-center 72. In this embodiment, the measured projections at the iso-channel will range from the minimum penetration length 80 to the maximum penetration length 84, as depicted in FIG. 3. If more than one spectral calibration scan is performed, one of the scans, typically the scan of the smallest phantom 70, can be offset to ensure satisfactory near-iso channel calibration while remaining calibration scans may instead be offset to a greater degree.

After the size and offset of the phantom 70 has been determined at steps 90 and 92, a calibration scan is performed at step 94. The calibration scan may consist of a single rotation of the source 12 and detector 22 about the offset phantom 70. Where desired, the calibration scan may also incorporate the desired bowtie filter to complement the selected phantom 70. The measured calibration projection data sets 96 that are acquired during the calibration scan of step 94 consists of one or more data points for each detector element for each available penetration length, i.e., the minimum penetration length 80 to the maximum penetration length 84.

The measured calibration projection data sets 96 may then be pre-processed, as depicted at step 98, to correct for various factors before they are used to extract spectral errors, including basic data correction and normalization to generate projections, as well as general beam-hardening. The beam-hardening is typically corrected by means of correction vectors based upon the bowtie filter length seen by each detector element. To produce projection data, the measured calibration data sets 96 may also be processed by subtracting the dark signal, normalizing to the air signal and monitor channels, then by taking the −log of the data. If desired, off-focal radiation correction may be applied. In one embodiment, to better express the obtained projections for reliable view fitting, for each view, the projections are squared to form the calibration projection data sets 100.

The pre-processed calibration projection data set 100 may then be farther processed to extract high-order calibration vectors 102, as depicted at step 104. For the purpose of discussion, the extraction step 104 is discussed in greater detail with reference to FIG. 5. In particular, as discussed below, projection value dependent spectral responses can be obtained by comparing the fitting of each projection view to the measured projection view from all of the view angles. The spectral responses obtained by the fitting process provide correction factors for different penetrations, thereby providing higher order corrections for different penetration lengths 78. In the extraction process, at each projection angle, the pre-processed calibration projection data set 100 is fitted with a known functional form representing the shape of the projection curve from a circular object. The difference between this fitting and the pre-processed calibration projection data set 100 is characterized as the spectral response for each detector channel. In one embodiment, the spectral response is captured as a function of a high-order polynomial for rapid correction.

Figure 5:
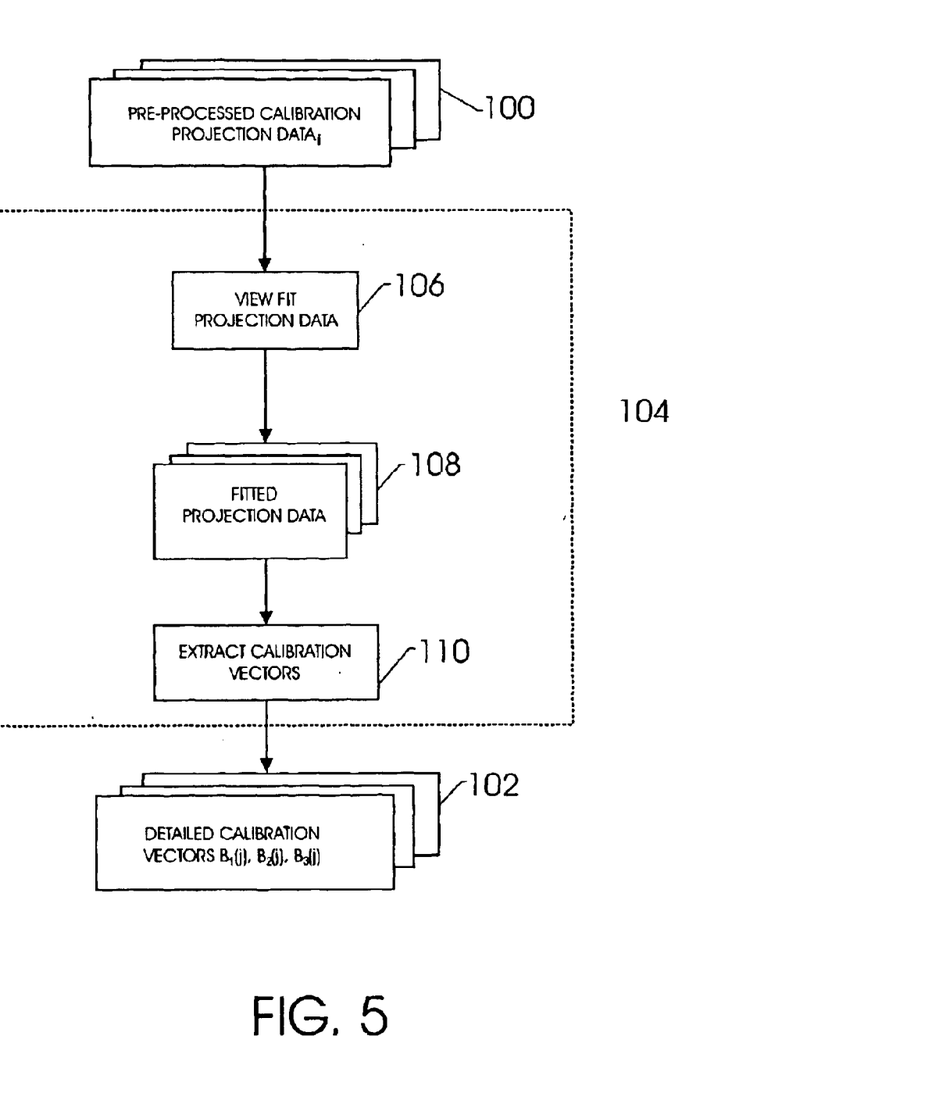
FIG. 5 is a flowchart depicting the step of extracting high order calibration vectors, as depicted in FIG. 4, in greater detail.

In particular, in the extraction step 104 a pre-processed calibration projection data set 100 is fitted according to a view fitting process or algorithm, as depicted by step 106, to produce a fitted projection data set 108. For example, in one embodiment in which uniform weighting is desired, the view function:

$$V_f = a[0] + a[1]*\sin[g(i)] + a[2]*\cos[g(i)] + a[3]*\sin[2*g(i)] + a[4]*\cos[2*g(i)] \quad (1)$$

may be employed where a[]'s are the fitting parameters, i is the detector element index and g(i) is two times the detector channel angle with respect to the line that connects the source 12 and the isocenter 72. In the above view function (1), the first three terms represent the ideal squared-projection curve for a circular phantom 70, while the last two terms account for slight deformation of the phantom 70 from a circular shape to an elliptical one, which might be due to defects in the phantom itself or misalignment during phantom positioning. To avoid fitting projection data at the phantom edge, which may lead to errors associated with the Lucite wall of the phantom 70 or due to off-focal radiation effects, a minimum projection data threshold, $L_{min}$, may be employed. For example, in one embodiment, a $L_{min}$ of 1.6 may be employed. In accordance with this threshold, the data pairs comprising the squared measured projection data greater than $L_{min}$ and the respective detector channel angles g(i) are fitted in accordance with the view function (1), yielding the fitted squared-projection data 108 for each detector element i.

The calibration vectors 102 may then be extracted from the fitted squared-projection data 108, as depicted by step 110 of FIG. 5. The extraction of the calibration vectors, may comprise fitting the measured projection data, $P(v, j)_{measured}$, 96 with the fitted projection data, $P(v, j)_{fitted}$, i.e., the square root of the fitted squared-projection data 108, with a polynomial function and no constant term. That is, $P(v, j)_{fitted} = F(P(v, j)_{measured})$. Typically, it is sufficient to use a third-order polynomial function. The result of the extraction process is one or more detailed calibration vectors 102 which provide spectral response correction to individual detector elements.

To cover more effective calibration range, a second phantom 70 may be calibrated as well. The second phantom calibration proceeds as discussed above to obtain a second set of calibration vectors. The respective polynomials from the first and second phantom calibrations may be combined to form new correction vectors that more reliably cover the entire projection range or a larger region of the projection range.

The detailed calibration vectors 102 from one or more phantom calibrations may be further processed to generate final spectral calibration vectors at step 112 which encompass the overall detector channel spectral response. In particular, the previously derived calibration coefficients may be combined to form a comprehensive calibration set of third or higher order polynomial coefficients for each detector element. In this way, the successive sets of correction vectors which might be applied to a set of uncorrected projection data can be combined into a single set of correction vectors, which may be used to form a spectral calibration transfer function 114 for rapid correction.

Figure 6:
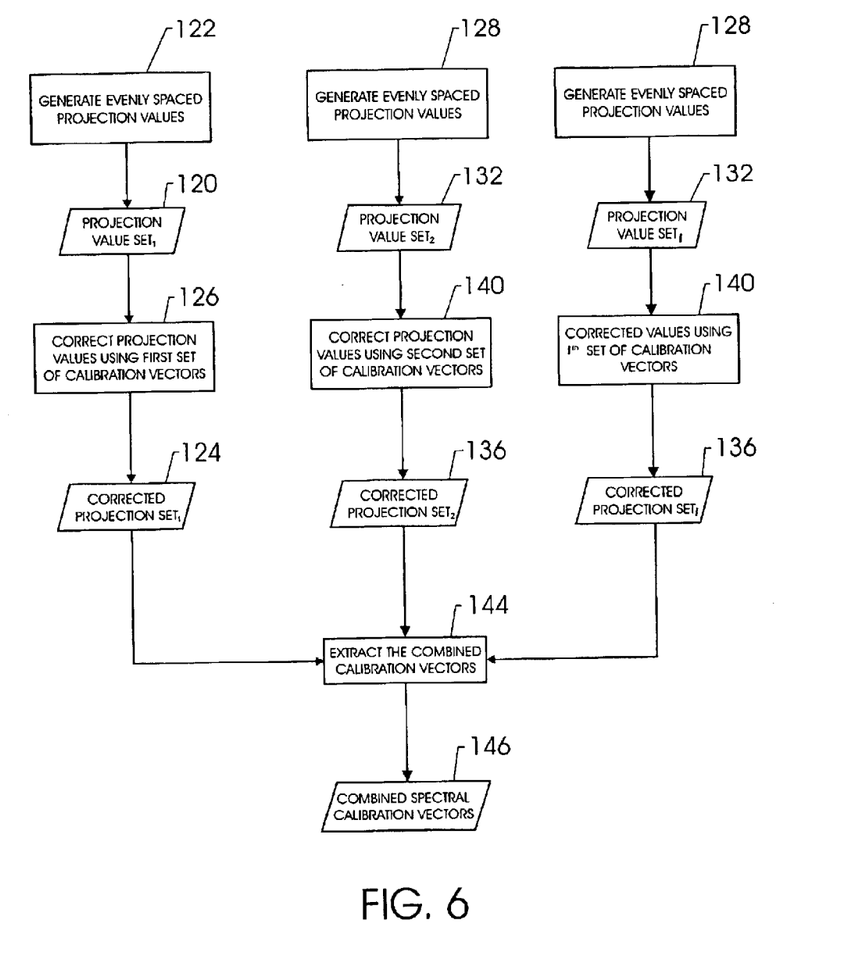
FIG. 6 is a flowchart depicting one embodiment in which multiple projection value sets are generated to allow the extraction of combined spectral calibration vectors.

In one embodiment, the combination of calibration vectors from more than one phantom calibration may be accomplished by performing the following steps for each detector element, as depicted in FIG. 6. A projection value set, $P(v,j)_1$, 120 is generated at evenly spaced projection values which cover the projection value range of a first phantom, $P(v, j)_1$, as depicted at step 122. Using the spectral calibration vector $F_1$ for the first phantom, a set of spectral corrected projection values 124 is generated at step 126, where $P_{fitted}(v, j)_1 = F_1(P(v,j)_1)$. Likewise, at steps 128, evenly spaced projection value sets 132 may be generated for each detector element using the calibration vectors derived from a second phantom, $P(v, j)_2$ and any additional phantoms, $P(v,j)_i$. Each projection value set 120, 132 covers the projection value range of the respective phantom used to generate the calibration vectors. Spectral corrected projection value sets 136 for the respective projection sets 132 are generated at steps 140, such that $P_{fitted}(v, j)_i = F_i(P(v,j)_i)$, where i indicates the respective phantom. At step 144 the computed projection length values may be used to extract the combined calibration vectors 146, by fitting the combined computed projection data, $P_{fitted}(v, j)_{1, 2, \ldots, i}$, with the evenly spaced projection data, $P(v,j)_{1, 2 \ldots, i}$, using a polynomial function with no constant term, that is, $P_{fitted}(v, j)_{1, 2 \ldots, i} = F(P(v,j)_{1, 2 \ldots, i})$. Typically, it is sufficient to use a third-order polynomial function. The resultant fit is the combined spectral calibration vectors 146.

Figure 7:
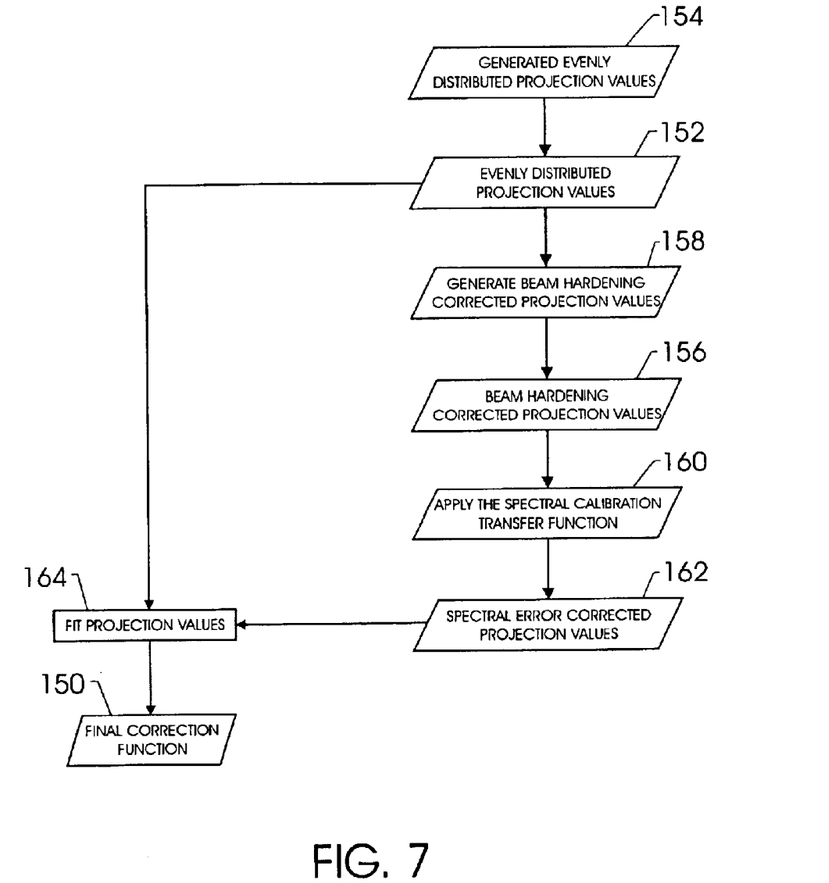
FIG. 7 is a flowchart depicting one embodiment in which a comprehensive, final correction function is determined.

A final correction function 150 may also be generated which addresses both detector-property independent beam-hardening correction and detector-property dependent spectral correction. Such a final correction function 150 may be desirable to save time in the correction process. In one embodiment of the present technique, a final correction function 150 may be generated by performing the following steps for each detector element, as depicted in FIG. 7. For each detector element, evenly distributed projection values 152 covering the desired range of projection length values of interest are generated as depicted at step 154. Beam-hardening corrected projection values 156 are generated based on the general beam-hardening correction function, as depicted at step 158. At step 160, spectral error corrected projection values 162 are generated by applying the spectral calibration transfer functions to the beam-hardening corrected projection values 156. The evenly distributed projection values 152 are then fitted with the projection values 162 corrected by both the general beam-hardening correction function and the spectral calibration transfer function, as depicted at step 164. The functional form of the fit can be a third or fourth order polynomial. The fitted polynomial is the final correction function 150, accounting for beam-hardening and spectral errors. For those detector channels far from the isocenter, i.e., far from the isochannel 82, which the spectral calibration phantom does not cover, the functional form of the final correction function 150 may be set to equal the beam hardening correction function.

By means of the above techniques, the spectral response of detector elements may be quickly and accurately captured on a channel-by-channel basis, allowing image artifacts attributable to differential spectral response between channels to be corrected. Due to the fact that the spectral errors captured are separated from beam hardening effects, it is possible that the phantom scans from different bowtie filters can be mixed, provided that the bowtie shape is smooth. For example, a small phantom can be used to calibrate the system for the bowtie designed for imaging human heads, and a large phantom for the bowtie designed for imaging the body.

Though the bowtie lengths are different, it is observed that combining the spectral errors from the two scans can provide an effective spectral correction for both the bowties.

While the above discussion relates steps to be performed in processing image date or in calibrating the spectral response of a suitable system, it is to be understood that the processing steps and calculations discussed may be implemented as automated routines, such as may be executed by a processor-based system. In particular, the processes and steps discussed may be implemented and stored as routines accessible to an imaging system 10 either locally or remotely. The routines may be stored on one or more tangible media, including magnetic media, such as tape, hard drive, memory chips, and so forth, and optical media, such as CD or DVD. In addition, different routines comprising the process may be stored at different locations or on different media.

While the invention may be susceptible to various modifications and alternative forms, specific embodiments have been shown by way of example in the drawings and have been described in detail herein. However, it should be understood that the invention is not intended to be limited to the particular forms disclosed. In particular, other imaging modalities which undergo spectral calibration to calibrate one or more detector elements may benefit from the above discussion. For example, non-invasive and non-destructive imaging techniques, such as those employed in baggage screening, industrial inspection, package testing, and materials analysis, may also benefit from the above techniques. The invention, therefore, is to cover all modifications, equivalents, and alternatives falling within the spirit and scope of the invention as defined by the following appended claims.

What is claimed is:

1. A method for calibrating a detector element of an imaging system, the method comprising:
   (a) positioning a calibration phantom offset from the isocenter of an imaging system;
   (b) performing a calibration scan of the offset calibration phantom;
   (c) acquiring a measured projection data set for a detector element of the imaging system;
   (d) pre-processing the measured projection data set to generate a calibration projection data set for the detector element; and
   (e) deriving a calibration vector for the detector element by fitting the calibration projection data set according to a view fitting technique.

2. The method as recited in claim 1, further comprising (f) correcting spectral response of the detector element by applying the calibration vector to a set of projection data acquired by the element.

3. The method as recited in claim 1, wherein pre-processing the measured projection data set comprises at least one of correcting for beam hardening, subtracting a dark signal, normalizing to an air signal, normalizing to a monitor channel, taking the negative log of the data, and correcting for off-focal radiation.

4. The method as recited in claim 1, wherein pre-processing the measured projection data set comprises squaring the measured projection data set to form the calibration projection data set.

5. The method as recited in claim 1, wherein deriving the calibration vector comprises comparing the calibration projection data set fitted to a known projection curve with the calibration projection data set, across a plurality of view angles.

6. The method as recited in claim 5, wherein the known projection curve represents an ideal projection form with no detector spectral errors.

7. The method as recited in claim 5, wherein the known projection curve is of a circular object.

8. The method as recited in claim 1, further comprising:
   (f) repeating steps (a) through (e) using one or more phantoms of different sizes.

9. The method as recited in claim 1, further comprising:
   (f) generating a transfer function for the detector element, wherein the transfer function incorporates the calibration vector for the detector element and one or more additional correction factors.

10. The method as recited in claim 9, wherein the one or more additional correction factors include at least one of a correction factor for beam hardening, for signal normalization, and for off-focal radiation.

11. The method as recited in claim 1, further comprising:
    (f) repeating steps (c) through (e) to derive a set of calibration vectors for a respective set of detector elements comprising a detector array.

12. The method as recited in claim 11, further comprising:
    (g) generating a projection value set using the set of calibration vectors;
    (h) generating one or more additional projection value sets using one or more respective sets of calibration vectors using one or more respective calibration phantoms of different sizes at step (a); and
    (i) extracting a set of combined spectral calibration vectors from the projection value set and the one or more additional projection value sets.

13. The method as recited in claim 1, further comprising:
    (f) generating a set of projection values for the detector element;
    (g) generating a set of beam hardening corrected projection values for the detector element;
    (h) correcting the set of beam hardening corrected projection values using the calibration vector to form a set of spectral error corrected projection values; and
    (i) comparing the set of projection values and the set of spectral error corrected projection values to derive a final correction function for the detector element.

14. The method as recited in claim 13, further comprising repeating steps (c) through (i) to derive a set of final correction functions for a respective set of detector elements comprising a detector array.

15. A computer-readable media, the computer-readable media comprising:
    a routine for performing a calibration scan of a calibration phantom offset from the iso-center of an imaging system;
    a routine for acquiring a measured projection data set for a detector element of the imaging system;
    a routine for pre-processing the measured projection data set to generate a calibration projection data set for the detector element; and
    a routine for deriving a calibration vector for the detector element by fitting the calibration projection data set according to a view fitting technique.

16. The computer-readable media as recited in claim 15, further comprising a routine for correcting spectral response of the detector element by applying the calibration vector to a set of projection data acquired by the element.

17. The computer-readable media as recited in claim 15, wherein the routine for pre-processing the measured projection data set performs at least one of correcting for beam hardening, subtracting a dark signal, normalizing to an air signal, normalizing to a monitor channel, taking the negative log of the data, and correcting for off-focal radiation.

18. The computer-readable media as recited in claim 15, wherein the routine for pre-processing the measured projection data squares the measured projection data set to form the calibration projection data set.

19. The computer-readable media as recited in claim 15, wherein the routine for deriving a calibration vector compares the calibration projection data set fitted to a known projection curve with the calibration projection data set, across a plurality of view angles.

20. The computer-readable media as recited in claim 19, wherein the known projection curve represents an ideal projection form with no detector spectral errors.

21. The computer-readable media as recited in claim 19, wherein the known projection curve is of a circular object.

22. The computer-readable media as recited in claim 15, further comprising a routine for generating a transfer function for the detector element, wherein the transfer function incorporates the calibration vector for the detector element and one or more additional correction factors.

23. The computer-readable media as recited in claim 22, wherein the one or more additional correction factors include at least one of a correction factor for beam hardening, for signal normalization, and for off-focal radiation.

24. The computer-readable media as recited in claim 15, wherein the routines for acquiring, pre-processing, and deriving are repeated to derive a set of calibration vectors for a respective set of detector elements comprising a detector array.

25. The computer-readable media as recited in claim 24, further comprising a routine for generating a projection value set using the set of calibration vectors, a routine for generating one or more additional projection value sets using one or more respective sets of calibration vectors derived from one or more respective calibration phantoms of different sizes, and a routine for extracting a set of combined spectral calibration vectors from the projection value set and the one or more additional projection value sets.

26. The computer-readable media as recited in claim 15, further comprising a routine for generating a set of projection values for the detector element, a routine for generating a set of beam hardening corrected projection values for the detector element, a routine for correcting the set of beam hardening corrected projection values using the calibration vector to form a set of spectral error corrected projection values, and a routine for comparing the set of projection values and the set of spectral error corrected projection values to derive a final correction function for the detector element.

27. The computer-readable media as recited in claim 26, wherein the routines for acquiring, pre-processing, deriving, generating, correcting, and comparing are repeated to derive a set of final correction functions for a respective set of detector elements comprising a detector array.

28. An imaging system, comprising:
a source of radiation;
a detector array comprising a plurality of detector elements, wherein each detector element is configured to detect radiation from the source;
a system controller configured to control the source and the detector array and to acquire data from the detector array;
a computer configured to communicate with the system controller, wherein the computer is configured to perform a calibration scan of a calibration phantom offset from the iso-center of the imaging system, to acquire a measured projection data set for each detector element of the imaging system, to pre-process the measured projection data sets to generate a calibration projection data set for each detector element, and to derive a calibration vector for each detector element by fitting the respective calibration projection data set according to a view fitting algorithm; and
an operator workstation configured to communicate with the computer.

29. The imaging system as recited in claim 28, wherein the computer is further configured to correct the spectral response of each detector element by applying the respective calibration vector to a set of projection data acquired by the detector array.

30. The imaging system as recited in claim 28, wherein the computer pre-processes the measured projection data sets by performing at least one of correcting for beam hardening, subtracting a dark signal, normalizing to an air signal, normalizing to a monitor channel, taking the negative log of the data, and correcting for off-focal radiation.

31. The imaging system as recited in claim 28, wherein the computer pre-processes the measured projection data sets by at least squaring the measured projection data set to form the calibration projection data set.

32. The imaging system as recited in claim 28, wherein the computer derives the calibration vectors by comparing the calibration projection data set for each element fitted to a known projection curve with the calibration projection data set for the respective element, across a plurality of view angles.

33. The imaging system as recited in claim 32, wherein the known projection curve represents an ideal projection form with no detector spectral errors.

34. The imaging system as recited in claim 32, wherein the known projection curve is of a circular object.

35. The imaging system as recited in claim 28, wherein the computer is further configured generate a transfer function for each detector element, wherein each transfer function incorporates the calibration vector for the respective detector element and one or more additional correction factors.

36. The imaging system as recited in claim 35, wherein the one or more additional correction factors include at least one of a correction factor for beam hardening, for signal normalization, and for off-focal radiation.

37. The imaging system as recited in claim 28, wherein the computer is further configured to generate a projection value set for each detector element using the set of calibration vectors, to generate one or more additional projection value sets for each detector element using one or more respective sets of calibration vectors derived from one or more respective calibration phantoms of different sizes, and to extract a combined spectral calibration vector for each detector element from the respective projection value set and the one or more respective additional projection value sets.

38. The imaging system as recited in claim 28, wherein the computer is further configured to generate a set of projection values for each detector element, to generate a set of beam hardening corrected projection values for each detector element, to correct each set of beam hardening corrected projection values using the respective calibration vector to generate a set of spectral error corrected projection values for each detector element, and to compare the set of projection values and the respective set of spectral error corrected projection values to derive a final correction function for each detector element.

39. The imaging system as recited in claim 28, further comprising a memory.

40. An imaging system, comprising:
means for performing a calibration scan of a calibration phantom offset from the iso-center of an imaging system;

means for acquiring a measured projection data set;

means for pre-processing the measured projection data set to generate a calibration projection data set; and means for deriving one or more calibration vectors by fitting the calibration projection data set according to a view fining algorithm.

41. The imaging system as recited in claim 40, further comprising means for correcting spectral response of the detector element.

42. The imaging system as recited in claim 40, wherein the means for pre-processing performs at least one of correcting for beam hardening, subtracting a dark signal, normalizing to an air signal, normalizing to a monitor channel, taking the negative log of the data, and correcting for off-focal radiation.

43. The imaging system as recited in claim 40, further comprising means for generating a transfer function for the detector element, wherein the transfer function incorporates the calibration vector for the detector element and one or more additional correction factors.

44. The imaging system as recited in claim 40, further comprising means for generating a projection value set using the one or more of calibration vectors, means for generating one or more additional projection value sets using one or more respective sets of calibration vectors derived from one or more respective calibration phantoms of different sizes, and means for extracting a set of combined spectral calibration vectors.

45. The imaging system as recited in claim 40, further comprising means for generating a set of projection values, means for generating a set of beam hardening corrected projection values, means for correcting the set of beam hardening corrected projection values using the one or more calibration vectors to form a set of spectral error corrected projection values, and means for deriving a final correction function for the detector element.

* * * * *